(12) United States Patent
Giesa et al.

(10) Patent No.: US 9,193,647 B2
(45) Date of Patent: Nov. 24, 2015

(54) PROCESS FOR PREPARING BUTADIENE AND/OR BUTENES FROM N-BUTANE

(71) Applicant: BASF SE, Ludwigshafen (DE)

(72) Inventors: Sonja Giesa, Darmstadt (DE); Regina Benfer, Altrip (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/752,516

(22) Filed: Jan. 29, 2013

(65) Prior Publication Data

US 2013/0211166 A1    Aug. 15, 2013

Related U.S. Application Data

(60) Provisional application No. 61/592,019, filed on Jan. 30, 2012.

(51) Int. Cl.
| | |
|---|---|
| *C07C 7/11* | (2006.01) |
| *C07C 5/333* | (2006.01) |
| *C07C 7/08* | (2006.01) |
| *C07C 5/48* | (2006.01) |

(52) U.S. Cl.
CPC . *C07C 7/11* (2013.01); *C07C 5/333* (2013.01); *C07C 5/48* (2013.01); *C07C 7/08* (2013.01)

(58) Field of Classification Search
USPC .......................................... 585/627, 628, 616
See application file for complete search history.

(56) References Cited

U.S. PATENT DOCUMENTS 7,488,857 B2 *   2/2009  Johann et al. ................. 585/325

2005/0171311 A1   8/2005  Schindler et al.
2007/0055088 A1 *  3/2007  Schindler et al. ............. 585/702

(Continued)

FOREIGN PATENT DOCUMENTS

| DE | 102004054766 A1 | 5/2006 |
|---|---|---|
| DE | 102004059356 A1 | 6/2006 |

(Continued)

OTHER PUBLICATIONS (2008). Knovel Critical Tables (2nd Edition). Knovel. Online version available at: http://app.knovel.com/hotlink/toc/id:kpKCTE000X/knovel-critical-tables.*

(Continued)

*Primary Examiner* — In Suk Bullock
*Assistant Examiner* — Aliz Z Fadhel
(74) *Attorney, Agent, or Firm* — Drinker Biddle & Reath LLP

(57) ABSTRACT

The process for preparing butadiene from n-butane comprises the steps of
  A) providing a feed gas stream a comprising n-butane;
  B) feeding the feed gas stream a comprising n-butane into at least one first dehydrogenation zone;
  C) compressing in at least one first compression stage and cooling the gas stream b;
  D) absorbing the butenes and the stream c2 comprising butadiene, n-butane, hydrogen and water vapor, with or without inert gases and with or without carbon oxides, with a selective solvent;
  E) extractively distilling the selective solvent;
  F) distilling the selective solvent;
  G) feeding stream f and an oxygenous gas into at least one second dehydrogenation zone and oxidatively dehydrogenating 1-butene and 2-butenes.

16 Claims, 3 Drawing Sheets

(56) References Cited

U.S. PATENT DOCUMENTS

Figure 3:
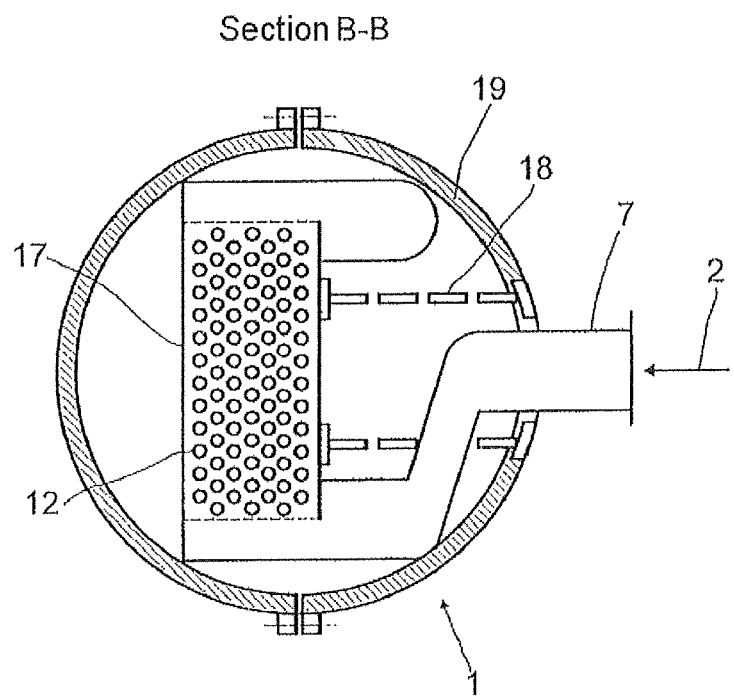

| | | | |
|---|---|---|---|
| 2007/0161842 | A1 | 7/2007 | Johann et al. |
| 2007/0244349 | A1 | 10/2007 | Crone et al. |
| 2008/0011968 | A1 | 1/2008 | Tanaka et al. |
| 2008/0097133 | A1 | 4/2008 | Crone et al. |
| 2008/0119680 | A1* | 5/2008 | Crone et al. .......... 585/633 |
| 2011/0118365 | A1 | 5/2011 | Steiner et al. |
| 2011/0130607 | A1 | 6/2011 | Kolios et al. |
| 2012/0157737 | A1 | 6/2012 | Olbert et al. |

FOREIGN PATENT DOCUMENTS

| | | |
|---|---|---|
| DE | 102004061514 A1 | 7/2006 |
| EP | 1682468 A1 | 7/2006 |
| SU | 1159915 A1 | 6/1985 |
| WO | WO-2004007408 A1 | 1/2004 |
| WO | WO-2005042449 A1 | 5/2005 |
| WO | WO-2005063657 A1 | 7/2005 |
| WO | WO-2006050969 A1 | 5/2006 |

OTHER PUBLICATIONS

Stichlmair, J. 2010. Distillation, 3. Processes. Ullmann's Encyclopedia of Industrial Chemistry.*

Raheleh Saffari, Fahimeh Abbasi, Farhang Jalali-Farahani and Navid Mostoufi. "Steady-State and Dynamic Simulation of the Process of Extractive Distillation of 1,3-Butadiebe From the C4-Cut". Proceedings of the 2005 International Conference on Simulation and Modeling.*

International Search Report in German for PCT/EP2013/051763, mailing date Apr. 16, 2013.

U.S. Appl. No. 13/411,080, filed Apr. 16, 2013, Kostova, et al.

Translation of the International Preliminary Report on Patentability for PCT/EP2013/051763 dated Aug. 5, 2014.

* cited by examiner

Figure 1
Figure 2
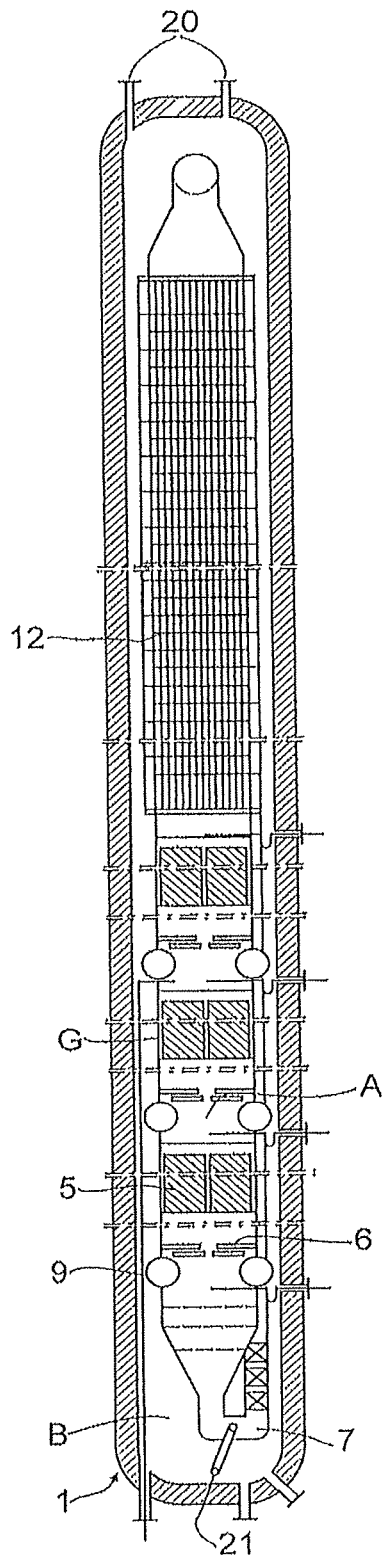
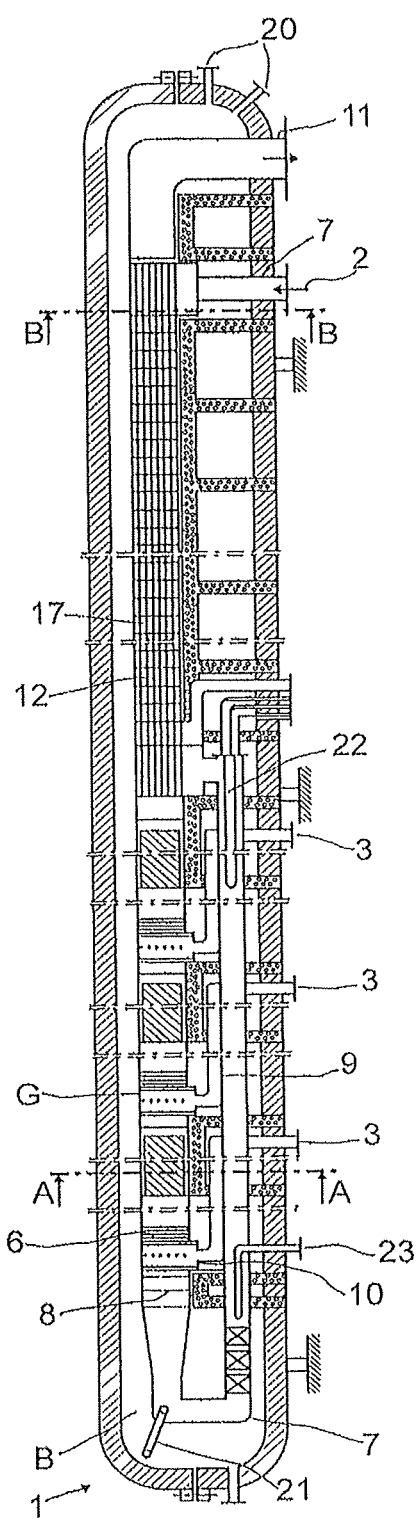

PROCESS FOR PREPARING BUTADIENE AND/OR BUTENES FROM N-BUTANE

CROSS-REFERENCE TO RELATED APPLICATIONS

This application claims the benefit of U.S. Provisional Application No. 61/592,019, filed Jan. 30, 2012, which is incorporated herein by reference.

The invention relates to processes for preparing butadiene or butenes from n-butane.

Butenes and butadiene can be prepared, for example, by steamcracking of saturated hydrocarbons, typically proceeding from naphtha as the raw material. The steamcracking of naphtha gives rise to a hydrocarbon mixture of methane, ethane, ethene, acetylene, propane, propene, propyne, allene, methylallene, $C_5$ hydrocarbons and higher hydrocarbons.

Butenes are understood to mean 1-butene, isobutene, 2-butenes and mixtures thereof. Butene streams comprise, for example, 30 to 80% by weight of butenes, for example 14% by weight of 1-butene, 10% by weight of isobutene, 15.5% by weight of trans-2-butene and 16.5% by weight of cis-2-butene. According to the invention, butenes are understood to mean 1-butene and 2-butenes.

A disadvantage of this process for obtaining butenes and butadiene is that relatively large amounts of unwanted coproducts are inevitably obtained. Alternatively, the butenes can be prepared from butane, and butadiene from n-butene, by dehydrogenation.

DE-A 10 2004 059 356 discloses, for example, that butadiene can be prepared using n-butane as a feedstock. To prepare the butadiene, the n-butane is dehydrogenated in a dehydrogenation zone by nonoxidative catalytic dehydrogenation into a stream comprising n-butane, 1-butene, 2-butene, butadiene and hydrogen, with or without carbon dioxide and with or without water vapor. The gas mixture obtained is cooled and then conducted directly into the next dehydrogenation zone. In a second dehydrogenation zone, the 1-butene and 2-butene are dehydrogenated further to butadiene. The stream obtained in the dehydrogenation is subsequently compressed and cooled in order to condense out water. From the residual stream comprising n-butane, butadiene, hydrogen, carbon dioxide and water vapor, a product stream comprising essentially butadiene is removed by extractive distillation.

A corresponding process for preparing butadiene from n-butane is additionally also described in DE-A 10 2004 061 514.

A disadvantage of the processes described here is that the second dehydrogenation zone directly follows the first. The composition of the inlet gas of the second dehydrogenation stage is therefore defined by the composition of the gas stream from the first dehydrogenation stage and cannot be optimized. The gas constituents present alongside the C4 hydrocarbons, such as nitrogen, steam, hydrogen, carbon monoxide and/or carbon dioxide, some of which are formed in the first dehydrogenation stage, are passed completely through the second dehydrogenation stage. The butane unconverted in the first dehydrogenation stage is recycled only after passing through the second dehydrogenation stage and the downstream workup stages. In this case, the butane is removed together with unconverted butenes and recycled into the first dehydrogenation stage. The recycling of butenes unconverted in the second dehydrogenation stage into the first dehydrogenation stage has an adverse effect on the butene yield therein. Another disadvantage is that the unconverted butane from the first dehydrogenation stage is likewise not removed in the inlet gas stream of the second dehydrogenation stage, or the butene content of this stream is adjusted by a depletion of the butane.

Removal of the hydrogen formed in the first dehydrogenation stage and utilization for provision of the energy required for the reaction by reaction with oxygen in the case of recycling into this stage is not possible here.

DE-A-10 2004 054 766 describes a process for preparing butadiene from n-butane, in which the stream comprising butadiene from the two-stage dehydrogenation is first cooled in order to condense out water. In a further compression stage and cooling, a condensate stream comprising n-butane, butadiene and water is obtained. From the stream comprising water, n-butane and butadiene, n-butane and butadiene are removed and then separated into a product stream consisting essentially of butadiene and a recycle stream comprising n-butane.

A disadvantage here is that the $C_4$ components are separated from the inert gases by a multistage compression and subsequent condensation. This process stage features a high energy demand for the compression to about 30 bar. The $C_4$ condensation is effected at a temperature of 10° C., and so a refrigeration system is additionally required. In addition, the product stream of the first dehydrogenation, again after cooling, is conducted directly into the second dehydrogenation.

It is an object of the present invention to provide a process for preparing a stream comprising butadiene and optionally a further stream comprising butene and butane proceeding from butane, which allows optimal utilization of the butane used and optimized operation of a second dehydrogenation stage.

The object is achieved by a process for preparing butadiene from n-butane, comprising the steps of A) providing a feed gas stream a comprising n-butane;

B) feeding the feed gas stream a comprising n-butane into at least one first dehydrogenation zone and nonoxidatively catalytically dehydrogenating n-butane to obtain a gas stream b comprising n-butane, 1-butene, 2-butenes, butadiene and hydrogen, with or without water vapor, with or without carbon oxides and with or without inert gases;

C) compressing in at least one first compression stage and cooling the gas stream b to obtain at least one condensate stream c1 comprising water and a stream c2 comprising butenes and butadiene, n-butane, hydrogen and water vapor, with or without carbon oxides and with or without inert gases;

D) absorbing the butenes and the stream c2 comprising butadiene, n-butane, hydrogen and water vapor, with or without inert gases and with or without carbon oxides, with a selective solvent, preferably a mixture comprising 80 to 97% by weight of N-methylpyrrolidone and 3 to 20% by weight of water, to obtain a stream d1 comprising selective solvent, preferably N-methylpyrrolidone, water, and butenes, butadiene and butane, with or without carbon dioxide, and a stream d2 comprising hydrogen, with or without inert gases and butane;

E) extractively distilling the stream d1 comprising selective solvent, preferably N-methylpyrrolidone, water, and butenes, butadiene and butane, with or without carbon oxides, with a selective solvent, preferably a stream e1 comprising 80 to 97% by weight of N-methylpyrrolidone and 3 to 20% by weight of water, to separate the stream d1 comprising selective solvent, preferably N-methylpyrrolidone, water, and butenes, butadiene and butane, with or without carbon oxides, into a stream e2 comprising selective solvent, preferably N-methylpyrrolidone, water, and butane, butenes and butadiene, and a stream e3 comprising essentially butane, with or without carbon oxides;

F) distilling the stream e2 comprising selective solvent, preferably N-methylpyrrolidone, water, butane and butenes, butadiene, to give a stream e1 comprising essentially selective solvent, preferably N-methylpyrrolidone and water, and a stream f comprising butane, butenes, butadiene;

G) feeding stream f and an oxygenous gas into at least one second dehydrogenation zone and oxidatively dehydrogenating 1-butene and 2-butenes to obtain a gas stream g comprising n-butane, unconverted 1-butene and 2-butenes, butadiene and water vapor, with or without carbon oxides, with or without hydrogen and with or without inert gases.

Carbon oxides are carbon dioxide, carbon monoxide or mixtures thereof. Preference is given to recycling stream d2 fully or partly into the first dehydrogenation zone B).

In stage G), it is possible to feed in an additional feed stream.

Preference is given to recycling stream e1 fully or partly into the absorption zone D) and the extractive distillation zone E).

Preference is given to recycling stream e3 fully or partly into stage A).

Preference is given to following stage G) with performance of the following stage H):

H) removing the residual oxygen (apart from small traces) present in gas stream g by means of a catalytic incineration stage in which the oxygen (apart from small traces) is reacted with a portion of or all of the hydrogen d2 removed beforehand and/or additionally supplied hydrogen to obtain an oxygen-depleted stream h.

Preference is given to following stage G) or H) with performance of the following stages I) to L):

I) compressing in at least one first compression stage and cooling the oxygen-depleted stream h or gas stream g to obtain at least one condensate stream i1 comprising water and a gas stream i2 comprising n-butane, 1-butene, 2-butenes, butadiene, hydrogen and water vapor, with or without carbon oxides and with or without inert gases;

J) removing the uncondensable and low-boiling gas constituents comprising hydrogen, oxygen, carbon oxides, the low-boiling hydrocarbons methane, ethane, ethene, propane, propene and inert gases as gas stream j2 from gas stream i2 to obtain a C4 product gas stream j1 consisting essentially of C4 hydrocarbons;

K) separating gas stream j1 by extractive distillation with a selective solvent, preferably a mixture comprising 80 to 97% by weight of N-methylpyrrolidone and 3 to 20% by weight of water into a stream k1 consisting essentially of or comprising butadiene and selective solvent, preferably such as N-methylpyrrolidone and a stream k2 comprising n-butane, butenes and water vapor, with or without inert gases;

L) distilling the selective solvent, preferably stream k1 comprising N-methylpyrrolidone, water and butadiene to give a stream l1 comprising essentially selective solvent, preferably N-methylpyrrolidone and water, and a stream l2 comprising butadiene.

Preference is given to following stage L) with performance of the following stage M):

M) purifying distillation of the stream l2 comprising butadiene in one or two columns, in which a stream m2 comprising butadiene is obtained and a gas stream m1 comprising more volatile impurities than butadiene and/or a bottom stream m3 comprising less volatile impurities than butadiene is/are removed.

Preference is given to recycling gas stream j2 fully or partly into the second dehydrogenation zone G).

Preference is given to recycling stream k2 fully or partly into the feed gas stream into stage A), absorption stage D), extraction stage E) and/or partly the second dehydrogenation zone G).

Preference is given to performing the removal in stage J) in two stages, by absorption with subsequent desorption.

Preference is given to recycling stream l1 fully or partly into stage K).

Preference is given to performing the nonoxidative catalytic dehydrogenation of n-butane autothermally while feeding in an oxygenous gas. The oxygenous gas may, for example, be air, oxygen-enriched air or oxygen of technical grade purity.

The feed stream a comprising n-butane may be obtained from liquefied petroleum gas (LPG).

The invention also relates to a process for preparing butenes from n-butane, in which process steps A) to F) as specified above are performed.

The process according to the invention allows optimal utilization of the butane used and optimized operation of a second dehydrogenation stage through the specified workup after the first dehydrogenation stage.

Suitable solvents for the present separation task are selective solvents whose affinity for $C_4$ hydrocarbons having single bonds increases in the direction toward $C_4$ hydrocarbons having double bonds and further toward conjugated double bonds and triple bonds, preferably dipolar and more preferably dipolar aprotic solvents. For apparatus reasons, preference is given to relatively noncorrosive or noncorrosive substances.

Suitable selective solvents for the process according to the invention are, for example, butyrolactone, nitriles such as acetonitrile, propionitrile, methoxypropionitrile, ketones such as acetone, furfurole, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, especially N-methylpyrrolidone. In general, alkyl-substituted lower aliphatic acid amides or N-alkyl-substituted cyclic acid amides are used. Particularly advantageous solvents are dimethylformamide, acetonitrile, furfurole, and especially N-methylpyrrolidone.

However, it is also possible to use mixtures of these solvents with one another, for example of N-methylpyrrolidone with acetonitrile, mixtures of these solvents with cosolvents such as water and/or tert-butyl ethers, for example methyl tert-butyl ether, ethyl tert-butyl ether, propyl tert-butyl ether, n- or isobutyl tert-butyl ether.

N-Methylpyrrolidone is particularly suitable, referred to in the present context in abbreviated form as NMP, preferably in aqueous solution, advantageously with 0 to 20% by weight of water.

According to the invention, preference is given to using, both as solvent for the absorption in step D) and as an extractant for the extraction in step E) and in step K), a mixture of 80 to 97% by weight of N-methylpyrrolidone and 3 to 20% by weight of water, preferably a mixture of 90 to 93% by weight of N-methylpyrrolidone and 7 to 10% by weight of water and especially a mixture of 91 to 92% by weight of N-methylpyrrolidone and 8 to 9% by weight of water, for example a mixture of 91.7% by weight of N-methylpyrrolidone and 8.3% by weight of water.

Compared to the production of butadiene by steamcracking, the process features high selectivity. No unwanted coproducts are obtained. There is no need for the complex removal of butadiene from the product gas mixture of the cracking operation.

The process according to the invention features particularly effective exploitation of the raw materials. For instance, losses of the n-butane raw material as a result of preferential recycling of unconverted n-butane from process stage E) into the first dehydrogenation stage are minimized. The n-butane is not (completely) conducted through process steps F) to J), as a result of which these apparatuses can be designed with a smaller size.

The separation of butene and butane after the first dehydrogenation stage and preferred recycling of butane achieves a higher conversion of butane to butene than in the case of recycling of a butane/butene mixture from the extractive distillation after the second dehydrogenation stage. Unconverted butene is preferably recycled into the second dehydrogenation stage. The partial removal of a butene-containing product stream with a butene content adjustable through the extractive distillation is possible here.

It is also possible to feed a butene-containing $C_4$ stream into the oxidative dehydrogenation stage G) in addition to stream f. This stream may originate from all butene-containing sources. Conceivable examples are FCC product streams, and butene-containing streams obtained by dimerization of ethylene.

Individual stages can be performed as described in DE-A-10 2004 059 356, DE-A-10 2004 054 766 and DE-A-10 2004 061 514.

Preferred procedures are described hereinafter:

In a first process part, A, a feed gas stream a comprising n-butane is provided. This typically proceeds from gas mixtures rich in n-butane, such as liquefied petroleum gas (LPG), as the raw material. LPG comprises essentially saturated $C_2$-$C_5$-hydrocarbons. In addition, it also comprises methane and traces of $C_5^+$ hydrocarbons. The composition of LPG may vary greatly. Advantageously, the LPG used comprises at least 10% by weight of n-butane.

Alternatively, an upgraded C4 stream from crackers or refineries can be used.

In one variant of the process according to the invention, the provision of the dehydrogenation feed gas stream comprising n-butane comprises the steps of A1) providing a liquefied petroleum gas (LPG) stream,
A2) removing propane and optionally methane, ethane and $C_5^+$ hydrocarbons (principally pentanes, and additionally hexanes, heptanes, benzene, toluene) from the LPG stream to obtain a stream comprising butanes (n-butane and isobutane),
A3) removing isobutane from the stream comprising butanes to obtain the feed gas stream comprising n-butane, and optionally isomerizing the isobutane removed to give an n-butane/isobutane mixture and recycling the n-butane/isobutane mixtures into the isobutane removal.

Propane and optionally methane, ethane and $C_5^+$ hydrocarbons are removed, for example, in one or more customary rectifying columns. For example, in a first column, low boilers (methane, ethane, propane) can be removed via the top, and, in a second column, high boilers ($C_5^+$ hydrocarbons) at the bottom of the column. A stream comprising butanes (n-butane and isobutane) is obtained, from which isobutane is removed, for example in a customary rectifying column. The remaining stream comprising n-butane is used as a feed gas stream for the downstream butane dehydrogenation.

The isobutane stream removed can be subjected to an isomerization. For this purpose, the stream comprising isobutane is fed into an isomerization reactor. The isomerization of isobutane to n-butane can be performed as described in GB-A 2018815. An n-butane/isobutane mixture is obtained, which is fed into the n-butane/isobutane separation column.

The isobutane stream removed can also be sent to a further use, for example for preparation of methacrylic acid, polyisobutene or methyl tert-butyl ether.

The feed gas stream a comprising n-butane comprises generally at least 60% by weight of n-butane, preferably at least 90% by weight of n-butane. In addition, it may also comprise $C_1$-$C_4$ hydrocarbons as secondary constituents.

In one process part, B, the feed gas stream comprising n-butane is fed into a dehydrogenation zone and subjected to a nonoxidative catalytic dehydrogenation. This involves partially dehydrogenating n-butane in a dehydrogenation reactor over a dehydrogenation-active catalyst to 1-butene and 2-butenes, also forming butadiene (1,3-butadiene). Additionally obtained are hydrogen and small amounts of methane, ethane, ethene, propane and propene. According to the mode of operation of the dehydrogenation, it is also possible for carbon oxides (CO, $CO_2$), water and inert gases, such as nitrogen, to be present in the product gas mixture of the nonoxidative catalytic n-butane dehydrogenation. In addition, unconverted n-butane is present in the product gas mixture.

One feature of the nonoxidative mode of operation compared to an oxidative mode of operation is that no free hydrogen is formed in the oxidative dehydrogenation.

The nonoxidative catalytic n-butane dehydrogenation can in principle be performed in all reactor types and modes of operation known from the prior art. A description of dehydrogenation processes suitable in accordance with the invention is also present in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

The nonoxidative catalytic butane dehydrogenation can be performed with or without oxygenous gas as a cofeed. It is preferably performed as an autothermal nonoxidative dehydrogenation with supply of oxygen as a cofeed. In the autothermal mode of operation, the heat required is produced directly in the reactor system by combustion of hydrogen and/or hydrocarbons in the presence of oxygen. It is additionally possible with preference to add a hydrogen-comprising cofeed. In at least one reaction zone, oxygen is additionally added to the reaction gas mixture of the n-butane dehydrogenation, and the hydrogen and/or hydrocarbon present in the reaction gas mixture is at least partly combusted, which generates at least a portion of the heat of dehydrogenation required in the at least one reaction zone directly in the reaction gas mixture. Preference is given to the mode of operation with pure oxygen. Oxygen can preferably be fed in as an oxygen/steam mixture or as an air/steam mixture. By virtue of the use of an oxygen/steam mixture, only small amounts of inert gases (nitrogen) are introduced into the overall process.

In general, the amount of the oxygenous gas added to the reaction gas mixture is selected such that the combustion of hydrogen present in the reaction gas mixture and of any hydrocarbons present in the reaction gas mixture and/or of carbon present in the form of coke generates the amount of heat required for the dehydrogenation of the butane. In general, the total amount of oxygen supplied, based on the total amount of butane, is 0.001 to 0.5 mol/mol, preferably 0.005 to 0.2 mol/mol, more preferably 0.05 to 0.2 mol/mol.

The hydrogen combusted to generate heat is the hydrogen formed in the catalytic butane dehydrogenation and optionally hydrogen added additionally as a hydrogenous gas to the reaction gas mixture. Preferably, a sufficient amount of hydrogen should be present that the molar ratio in the reaction gas mixture immediately after the feeding of oxygen is 1 to 10, preferably 2 to 5 mol/mol. In the case of multistage reactors, this applies to each intermediate feeding of oxygenous, and optionally hydrogenous, gas.

The hydrogen is combusted catalytically. The dehydrogenation catalyst used generally also catalyzes the combustion of the hydrocarbons and of hydrogen with oxygen, and so in principle no specific oxidation catalyst is required. Suitable catalysts are described, for example, in DE-A 10 2004 061 514.

Suitable reactors are all reactors known to those skilled in the art for use of heterogeneous catalysts for gas-solid catalysis.

In one embodiment of the process according to the invention, there is intermediate feeding of oxygenous gas and hydrogenous gas upstream of each stage of a staged reactor. In a further embodiment of the process according to the invention, oxygenous gas and hydrogenous gas are fed in upstream of every stage except the first stage. In one embodiment, beyond each feed point, a layer of a specific oxidation catalyst is present, followed by a layer of the dehydrogenation catalyst. In a further embodiment, no specific oxidation catalyst is present. Suitable catalysts are also described, for example, in DE-A 10 2004 061 514; see also WO 2009/124974 and WO 2009/124945. The dehydrogenation temperature is generally 400 to 1100° C., the pressure in the outlet of the reactor generally 0.2 to 5 bar, preferably 1 to 3 bar. The space velocity (GHSV) is generally 500 to 2000 $h^{-1}$, and in high-load mode even up to 100 000 $h^{-1}$, preferably 4000 to 16 000 $h^{-1}$.

Other reactors, such as monolith reactors, are also suitable.

Preference is given to a reactor (1) in the form of a horizontal cylinder or prism for performance of an autothermal gas phase dehydrogenation of a butane-containing gas stream (2) with an oxygen-comprising gas stream (3) to obtain a reaction gas mixture over a heterogeneous catalyst configured as a monolith (4), wherein
the interior of the reactor (1) is divided by a circular cylindrical or prismatic gas-tight housing G arranged in longitudinal direction of the reactor (1) into
an inner region A with one or more catalytically active zones (5), in each of which is provided a packing composed of monoliths (4) stacked one on top of another, one alongside another and one behind another, and a mixing zone (6) with solid internals is provided upstream of each catalytically active zone (5), and
an outer region B arranged coaxially with respect to the inner region A, and
a heat exchanger (12) provided at one end of the reactor, connected to the housing G,
has one or more feed lines (7) for the butane-containing gas stream (2) to be dehydrogenated,
has one or more feed lines (9) which can be regulated independently of one another, each feed line (9) supplying one or more distributor chambers (10), for the oxygen-comprising gas stream (3) into each of the mixing zones (6), and
has a removal line (11) for the reaction gas mixture of the autothermal gas phase dehydrogenation, wherein
the outer region B is charged with a gas which is inert under the reaction conditions of the autothermal gas phase dehydrogenation and
the butane-containing gas stream (2) to be dehydrogenated is introduced into the heat exchanger (12) via a feed line (7), heated in the heat exchanger (12) by the reaction gas mixture by indirect heat exchange in countercurrent and conducted onward to the opposite end of the reactor to the heat exchanger (12), deflected there, introduced via a flow conditioner (8) into the inner region A, and mixed in the mixing zones (6) with the oxygen-comprising gas stream (3), and then the autothermal gas phase dehydrogenation takes place in the inner region A of the reactor (1).

The gas which is inert under the reaction conditions of the autothermal gas phase dehydrogenation is preferably water vapor.

Preference is given to conducting the gas which is inert under the reaction conditions of the autothermal gas phase dehydrogenation through the outer region B as a purge gas stream with a mass flow rate of 1/5 to 1/100, preferably 1/10 to 1/50, based on the mass flow rate of the butane-containing gas stream (2) under a low gage pressure of 2 to 50 mbar, preferably of 25 to 30 mbar, based on the pressure in the inner region A, preferably by introducing the purge gas stream into the outer region B of the reactor at one end of the reactor via one or more feed lines (20) and conducting it onward at the opposite end of the reactor into the inner region A of the reactor, more particularly via one or more connecting line(s) (21) arranged advantageously at an angle other than 90° to the feed line (7) for the butane-containing gas stream (2) to be dehydrogenated.

Preference is given to introducing the butane-containing gas stream (2) to be dehydrogenated into the heat exchanger (12) at two or more sites, preferably as a main stream with relatively high mass flow rate and one or more secondary streams with lower mass flow rate relative to the main stream.

Preference is given to providing, in addition to the heat exchanger (12), one or more additional heating means for the butane-containing gas stream (2) to be dehydrogenated.

Preference is given to providing, as the additional heating means for the butane-containing gas stream (2), the supply of hydrogen via a line (23) into the feed line (7) for the butane-containing gas stream (2) to be dehydrogenated, very close to the inlet into the mixing zones (6) arranged upstream of each catalytically active zone (5), and the additional heating means provided may be an electrical heater (22), which is preferably introduced in detachable form, as an inserted system, within the outer region B of the reactor (1), or as a muffle burner (22) into the feed line (7) for the butane-containing gas stream (2) to be dehydrogenated downstream of the exit thereof from the heat exchanger (12).

Preference is given to providing, in the inner region A, two or more catalytically active zones (5) each with a packing composed of monoliths (4) stacked one on top of another, one alongside another and one behind another.

Two or more of the reactors (1) may be used, in which case at least one reactor (1) is utilized for the autothermal gas phase dehydrogenation and, at the same time, at least one further reactor (1) is regenerated.

The regeneration is performed preferably within a temperature range between 550 and 700° C.

The regeneration is preferably performed with an oxygenous gas stream comprising 0.1 to 1.5% by weight of oxygen, based on the total weight of the oxygenous gas stream.

In this reactor,
the interior of the reactor is divided by a circular cylindrical or prismatic, gas-tight housing G arranged detachably in longitudinal direction of the reactor into
an inner region A with one or more catalytically active zones, in each of which a packing composed of monoliths stacked one top of another, one alongside another and one behind another, and a mixing zone with solid internals is provided upstream of each catalytically active zone, and an outer region B arranged coaxially with respect to the inner region A, wherein a heat exchanger provided at one end of the reactor, connected to the housing G, has one or more feed lines for the butane-containing gas stream to be dehydrogenated, has one or more feed lines which can be regulated independently of one another, each feed line supplying one or more distributor chambers, for the oxygen-comprising gas stream into each of the mixing zones, and has a removal line for the reaction gas mixture of the autothermal gas phase dehydrogenation, wherein the outer region B is charged with a gas which is inert under the reaction conditions of the autothermal gas phase dehydrogenation and the butane-containing gas stream to be dehydrogenated is introduced through a feed line into the heat exchanger, heated by indirect heat exchange by the reaction gas mixture in countercurrent and conducted onward to the opposite end of the reactor to the heat exchanger, deflected there, introduced via a flow conditioner into the inner region A, and mixed in the mixing zones with the oxygen-comprising gas stream, and then the autothermal gas phase dehydrogenation takes place in the inner region A of the reactor.

The autothermal gas phase dehydrogenation takes place over a heterogeneous catalyst which is in the form of monoliths.

According to the invention, the individual monoliths are stacked one alongside another, one on top of another and one behind another, in the required number to fill a catalytically active zone to form a packing.

Upstream of each packing is provided a mixing zone with solid internals which are not catalytically active. In the mixing zone, the butane-containing gas stream is mixed with the oxygen-comprising stream, the oxygen-comprising gas stream being mixed with the butane-containing feed stream in the first mixing zone at which flow arrives in flow direction, and an oxygen-comprising gas stream is fed intermediately into the butane-comprising reaction mixture still to be dehydrogenated in each of the downstream mixing zones.

The butane-containing gas stream to be dehydrogenated can preferably be introduced into the heat exchanger at two or more sites, more particularly as a main stream with relatively high mass flow rate and one or more secondary streams with lower mass flow rate compared to the main stream.

Figure 4:
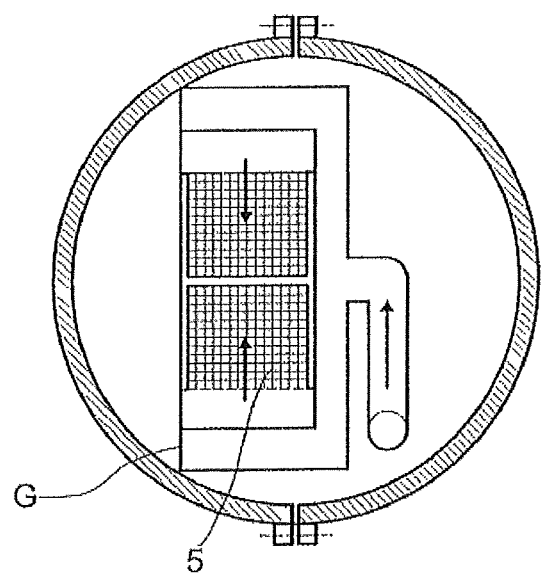
Figure 5:
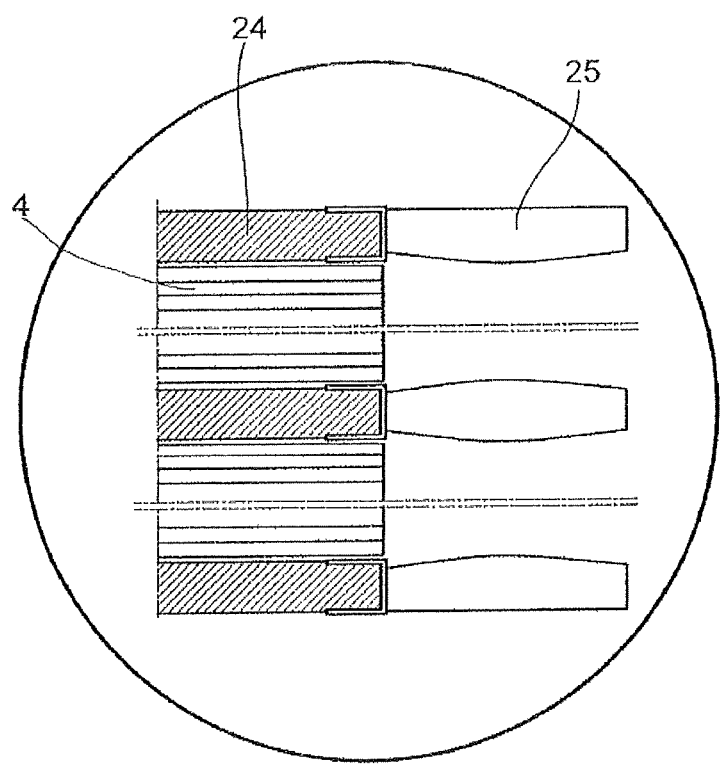

The individual drawings show:

FIG. 1 a longitudinal section through a preferred embodiment of an inventive reactor in the horizontal plane, FIG. 2 a longitudinal section through the same reactor in the vertical plane, FIG. 3 a cross section through the reactor shown in FIG. 2 in the B-B plane, FIG. 4 a cross section through the reactor shown in FIG. 2 in the A-A plane and FIG. 5 an enlargement of the region encircled in FIG. 1.

In the figures, identical reference symbols denote identical or corresponding features.

The longitudinal section in the horizontal plane in FIG. 1 shows, in schematic form, a preferred embodiment of a reactor 1 which is fed with a butane-containing gas stream 2 to be dehydrogenated via a feed line 11, and with an oxygen-comprising gas stream 3 via the feed lines 9. FIG. 1 shows that the housing G divides the interior of the reactor 1 into an inner region A and an outer region B. The inner region A is connected to a heat exchanger 12 at one end thereof. On the right-hand side of the drawing are shown feed lines 20 for the purge gas stream and, on the left-hand side, a connecting line 21 for the purge gas stream from the outer region B of the reactor into the feed line 7 for the butane-containing gas stream 2 to be dehydrogenated. Via the feed lines 20, a purge gas stream is introduced into the outer region B, and, via a connecting line 21 at the other end of the reactor, conducted onward into the inner region A via the feed line 7 for the butane-containing gas stream 2 to be dehydrogenated.

FIG. 2 shows additional heating means which can be used advantageously: an electrical heater 22 and a feed line 23 for hydrogen as combustion gas into the feed line 7 for the butane-containing gas stream 2 to be dehydrogenated.

FIG. 3 shows a cross-sectional diagram of the B-B plane in the region of the heat transferer. The figure illustrates the feeding of the butane-containing gas stream 2 to be dehydrogenated via feed line 7 into the intermediate space between the tubes 17 of the preferred embodiment of a shell and tube heat exchanger 12 shown in the figure.

In the cross-sectional diagram, the support construction 18 for the shell and tube heat exchanger 12 is likewise evident, which is preferably formed from perforated sheets, as are the insulation layer 19 of the inner wall of the reactor casing and the electrical heater 22 which is preferably used as an additional heating means.

FIG. 4 shows a further cross-sectional diagram in the A-A plane in the region of a reaction zone. The figure shows, more particularly, the feed line 23 for combustion gas.

The section shown in FIG. 5 illustrates the steel profiles 25 which are assigned in an extension of the expandable mats 24, which are clamped in U-shaped profiles made of high-temperature-resistant fabrics, and which adjoin the expandable mats 24 with a corresponding cross section and broaden to an increasing degree. Reference numeral 4 in FIG. 5 denotes the monoliths.

The butane dehydrogenation is generally preferably conducted in the presence of water vapor. The water vapor added serves as a heat carrier and promotes the gasification of organic deposits on the catalysts, which counteracts the coking of the catalysts and increases the service life of the catalysts. At the same time, the organic deposits are converted to carbon monoxide, carbon dioxide and possibly water.

The nonoxidative catalytic n-butane dehydrogenation affords a gas mixture which, as well as butadiene, 1-butene, 2-butenes and unconverted n-butane, generally comprises secondary constituents. Typical secondary constituents are hydrogen, water vapor, $CO_2$ and low boilers (methane, ethane, ethene, propane and propene). The composition of the gas mixture leaving the first dehydrogenation zone may vary significantly depending on the mode of operation of the dehydrogenation. For instance, in the case of performance of the preferred autothermal dehydrogenation with feeding of oxygen and additional hydrogen, the product gas mixture has a comparatively high content of water vapor and carbon oxides. In modes of operation without feeding of oxygen, the product gas mixture of the nonoxidative dehydrogenation has a comparatively high content of hydrogen.

The product gas stream of the nonoxidative autothermal n-butane dehydrogenation comprises preferably 0.1 to 15% by volume of butadiene, 1 to 15% by volume of 1-butene, 1 to 25% by volume of 2-butene (cis/trans-2-butene), 20 to 70% by volume of n-butane, 1 to 70% by volume of water vapor, 0 to 10% by volume of low-boiling hydrocarbons (methane, ethane, ethene, propane and propene), 0.1 to 40% by volume of hydrogen, 0 to 10% by volume of inert gas (nitrogen) and 0 to 5% by volume of carbon oxides, where the total amount of the constituents is 100% by volume.

The product gas stream b leaving the first dehydrogenation zone can, after compression in process stage C), be separated into two substreams in process stage D), in which case only one of the two substreams is subjected to the further process parts, E) to M), and the second substream is recycled into the first dehydrogenation zone. A corresponding procedure is described in DE-A 102 11 275. However, it is also possible to subject the entire product gas stream b of the nonoxidative catalytic n-butane dehydrogenation to the further process parts, E) to M).

In process stage C), the gas stream b is preferably first cooled. The compressed gas is cooled with heat exchangers, which may be designed, for example, as shell and tube, spiral or plate heat exchangers. The heat removed is preferably utilized for thermal integration in the process. Subsequently, in a preferred embodiment of process step C), water is removed from the product stream. The water is preferably removed in a quench.

Subsequently, gas stream c is compressed in at least one first compression stage and subsequently cooled, in the course of which at least one condensate stream c1 comprising water is condensed out to leave a gas stream c2 comprising n-butane, 1-butene, 2-butenes, butadiene, hydrogen, water vapor, and small amounts of methane, ethane, ethene, propane and propene, with or without carbon oxides and with or without inert gases.

The compression can be effected in one or more stages. Overall, compression is effected from a pressure in the range from 1.0 to 4.0 bar to a pressure in the range from 3.5 to 20 bar. Each compression stage is followed by a cooling stage in which the gas stream is cooled to a temperature in the range from 15 to 60° C. Condensate stream c1 may thus also comprise several streams in the case of multistage compression.

Gas stream c2 generally consists essentially of $C_4$ hydrocarbons (essentially n-butane, 1-butene and 2-butenes), hydrogen, carbon dioxide and water vapor. In addition, stream c2 may also comprise low boilers, butadiene and inert gases (nitrogen) as further secondary components. Condensate stream c1 generally consists to an extent of at least 80% by weight, preferably to an extent of at least 90% by weight, of water, and additionally comprises, to a minor extent, low boilers, $C_4$ hydrocarbons, oxygenates and carbon oxides.

Suitable compressors are, for example, turbo compressors, rotary piston compressors and reciprocating piston compressors. The compressors can be driven, for example, with an electric motor, an expander or a gas or steam turbine. Typical compression ratios (exit pressure:inlet pressure) per compressor stage are between 1.5 and 3.0, according to the design.

The compressed gas is cooled with heat exchangers, which may be designed, for example, as shell and tube, spiral or plate heat exchangers. The coolants used in the heat exchangers are generally cooling water or heat carrier oils. In addition, it is possible with preference to use air cooling, with use of blowers.

The absorption in step (D) can be performed in any desired suitable absorption column known to those skilled in the art. Preference is given to performing the absorption in countercurrent. For this purpose, the stream comprising butenes, butadiene, butane, hydrogen and inert gas (nitrogen), with or without carbon oxides, is supplied to the absorption column in the lower region. In the upper region of the adsorption column, the stream comprising N-methylpyrrolidone and water is introduced.

At the top of the absorption column, a hydrogen-rich and/or inert gas-rich (nitrogen-rich) stream d2 is withdrawn, which may also comprise residues of $C_4$ hydrocarbons and possibly carbon oxygenates. In addition, this stream may comprise inerts (for example, nitrogen) and low boilers (ethane, ethene, propane, propene, methane). The stream comprising N-methylpyrrolidone and water cools the supplied stream comprising butenes and/or butadiene, butane, hydrogen and/or inert gas (nitrogen), with or without carbon oxides, and at the same time preferentially absorbs the $C_4$ components and some carbon oxides. In some cases, small amounts of $H_2$, inerts ($N_2$) and low boilers are also absorbed. This stream is drawn off at the bottom of the absorption column.

The use of a mixture of N-methylpyrrolidone and water as a solvent for the absorption and as an extractant in the extractive distillation has the advantage that the boiling point is lower than the boiling point in the case of use of pure N-methylpyrrolidone. A further advantage is that increasing the water content in the mixture of water and N-methylpyrrolidone used as the solvent can enhance the selectivity. However this leads as expected to a reduction in the capacity. A further advantage is the selectivity of the N-methylpyrrolidone for carbon oxides, especially carbon dioxide. This enables, in addition to the removal of the hydrocarbons, a removal of the carbon oxides, especially of the carbon dioxide, from the hydrogen.

The absorption in step D) is performed generally at a bottom temperature in the range from 30 to 160° C., a top temperature in the range from 5 to 60° C., and a pressure in the range from 2 to 20 bar. Preference is given to performing the absorption at a bottom temperature in the range from 30 to 100° C., a top temperature in the range from 25 to 50° C. and a pressure in the range from 8 to 15 bar.

The absorption column is preferably a column with random packing or a column with structured packing. However, any other column is also conceivable, for example a tray column. A column suitable for the absorption preferably has 2 to 40 theoretical plates, preferably 5 to 25 theoretical plates.

The temperature of the stream which comprises N-methylpyrrolidone and water, for example e1 and/or 11, and is supplied to the absorption column is preferably 10 to 70° C., more preferably 20 to 40° C. The temperature of the stream comprising butenes, butadiene, butane, hydrogen and/or inert gas (nitrogen), with or without carbon oxides, is preferably in the range between 0 and 400° C., especially in the range between 40 and 200° C.

The ratio of N-methylpyrrolidone used to the stream comprising butenes, butadiene, butane, hydrogen and/or inert gas, with or without carbon oxides, is preferably in the range from 2 to 30, more preferably in the range from 4 to 30 and especially in the range from 4 to 15, based in each case on the masses of the streams used.

The stream d1 which comprises N-methylpyrrolidone, water, butenes, butadiene, butane and carbon oxides and is obtained in the absorption, comprises generally 20 to 90 mol % of N-methylpyrrolidone, 0 to 50 mol % of water, 0 to 20 mol % of butadiene, 0 to 20 mol % of 1-butene, 0 to 20 mol % of 2-butenes, 0 to 50 mol % of butane and 0 to 20 mol % of carbon oxides.

The stream d1 which comprises N-methylpyrrolidone, water, butenes, butadiene, butane and carbon oxides and is obtained in the absorption is then supplied to an extractive distillation in step (E).

The extractive distillation can be performed, for example, as described in Erdöl and Kohle Erdgas—Petrochemie volume 34 (8), pages 343 to 346 or Ullmanns Enzyklopädie der technischen Chemie, volume 9, 4th edition 1975, pages 1 to 18.

In the extractive distillation, the stream d1 comprising butenes, butadiene, butane, methylpyrrolidone, water and carbon oxides is contacted with a stream comprising N-methylpyrrolidone and water in an extractive distillation zone. The extractive distillation zone is generally configured in the form of a column which has trays, random packings or structured packings as internals. The extractive distillation zone has generally 10 to 70 theoretical plates, in order that a sufficiently good separating effect is achieved. The extraction column preferably has a rescrubbing zone in the top of the column. This rescrubbing zone serves for recovery of the N-methylpyrrolidone present in the gas phase by means of a liquid hydrocarbon return stream, for which the top fraction is condensed beforehand. Typical temperatures at the top of the column are between 30 and 60° C.

The top product stream e3 of the extractive distillation column comprises butane and carbon oxides and is drawn off in gaseous form. In addition to butane and carbon oxides, it is also possible for butenes, hydrogen and/or inert gas and other low boilers to be present in the top product stream. In a preferred embodiment, the top product stream e3 is condensed in order to remove carbon oxides such as $CO_2$ and any hydrogen and/or inert gas and low boilers present from butane. The liquid butane stream can, for example, be recycled into the dehydrogenation zone in process step B).

At the bottom of the extractive distillation column, a stream e2 comprising N-methylpyrrolidone, water, butenes, butane and butadiene is obtained. By removing a portion of the butane overhead, the butenes are concentrated here in stream e2. The degree of concentration is adjustable through the parameters of the column.

The stream e2 comprising N-methylpyrrolidone, water, butane, butenes and butadiene which is obtained at the bottom of the extractive distillation column, is fed to a distillation column F) in which a stream f consisting essentially of butenes, butane and butadiene is obtained overhead. At the bottom of the distillation column, a stream e1) comprising N-methylpyrrolidone and water is obtained, the composition of the stream comprising N-methylpyrrolidone and water corresponding to the composition as added to the absorption and the extraction. The stream comprising N-methylpyrrolidone and water is preferably divided and passed back into the absorption in process step D) and the extractive distillation in process step E). The ratio of the mixture of water and N-methylpyrrolidone which is supplied to the absorption to the mixture of water and N-methylpyrrolidone and $C_4$ which is supplied to the extractive distillation is preferably in the range from 0.2 to 20, especially in the range from 0.3 to 15.

The stream f removed overhead can be partly or fully drawn off from the plant and used as a product stream. The butene content can be adjusted via the mode of operation of the extractive distillation. A high butene concentration reduces the amount of butane which has to be conducted through process step G) and the subsequent process steps. At the same time, this increases the yield of the BDH stage.

The extractive distillation is operated preferably at a bottom temperature in the range from 90 to 250° C., especially at a temperature in the range from 90 to 210° C., a top temperature in the range from 10 to 100° C., especially in the range from 20 to 70° C., and a pressure in the range from 1 to 15 bar, especially in the range from 3 to 8 bar. The extractive distillation column preferably has 5 to 70 theoretical plates.

The distillation in process step (F) is preferably performed at a bottom temperature in the range from 100 to 300° C., especially in the range from 150 to 200° C., and a top temperature in the range from 0 to 70° C., especially in the range from 10 to 50° C. The pressure in the distillation column is preferably in the range from 1 to 10 bar. The distillation column has preferably 2 to 30 and especially 5 to 20 theoretical plates.

As well as the stream f obtained from process step F), it is also possible to supply further n-butene-containing streams to the ODH stage in process step G), as obtained, for example, in refineries from FCC units or by dimerization of ethylene. According to the invention, the addition of any n-butene-containing stream is conceivable.

The butene dehydrogenation can be operated as a single process or in combination with a butane dehydrogenation. The butene dehydrogenation can be operated nonoxidatively or oxidatively (with an $O_2$-rich gas as the oxidizing agent).

In the oxidative (catalytic) dehydrogenation in process step G), essentially 1-butene and 2-butenes are dehydrogenated to 1,3-butadiene, and 1-butene is generally depleted virtually completely.

The oxidative dehydrogenation can in principle be performed in all reactor types known from the prior art and by known modes of operation, for example in a fluidized bed, in a staged furnace, in a fixed bed tubular reactor or shell and tube reactor, or in a plate heat exchanger reactor. For performance of the oxidative dehydrogenation, a gas mixture having a molar oxygen:n-butenes ratio of at least 0.5 is preferably required. Preference is given to working at an oxygen:n-butenes ratio of 0.55 to 50, preferably 0.55 to 10, especially 0.55 to 3. To establish this value, in general, the product gas mixture originating from the nonoxidative catalytic dehydrogenation is mixed with pure oxygen or an oxygenous gas, directly or after a workup in which butenes are concentrated and hydrogen is removed. In one embodiment of the process, the oxygenous gas is air. The oxygenous gas mixture obtained is then sent to the oxydehydrogenation. A preferred alternative to the use of air is to use additional nitrogen or lean air with a proportion of less than 23% by volume as the oxygenous gas. In a preferred embodiment, the off gas from process step J), stream j2, is mixed with stream f and optionally additional steam, and sent to process step G). Thus, the amount of nitrogen which may be required for dilution of stream f can be reduced or rendered superfluous.

The catalysts particularly suitable for the oxydehydrogenation are based generally on an Mo—Bi—O-containing multimetal oxide system, which generally additionally comprises iron. In general, the catalyst system comprises further additional components from group 1 to 15 of the Periodic Table, for example, potassium, magnesium, zirconium, chromium, nickel, cobalt, cadmium, tin, lead, germanium, lanthanum, manganese, tungsten, phosphorus, cerium, aluminum or silicon.

Suitable catalysts and preparation thereof are described, for example, in U.S. Pat. No. 4,423,281, U.S. Pat. No. 4,336,409, DE-A-2600128 and DE-A-2440329, and also WO 2009/124974 and WO 2009/124945.

The catalyst for oxydehydrogenation is generally used in the form of shaped bodies having a mean size of more than 2 mm. Due to the pressure drop during the execution of the process, which has to be noted, relatively small shaped bodies are generally unsuitable. Examples of suitable shaped bodies include tablets, cylinders, hollow cylinders, rings, spheres, strands, wagon wheels or extrudates. Particular shapes, for example "Trilobes" and "Tristars" (see EP-A-0 593 646), or shaped bodies with at least one notch on the outside (see U.S. Pat. No. 5,168,090), are likewise possible.

In general, the catalyst used can be used in the form of what is called an unsupported catalyst. In this case, the entire shaped catalyst body consists of the active composition, including any assistants, for instance graphite or pore formers, and further components. In addition, it is possible to apply the active compositions of the catalysts to a support, for example an inorganic, oxidic shaped body, including any assistants, for instance graphite or pore formers, and further components. Such catalysts are generally referred to as eggshell catalysts.

The oxydehydrogenation is performed generally at a temperature of 220 to 490° C. and preferably from 250 to 450° C. A reactor inlet pressure sufficient to overcome the flow resistances existing in the plant and the downstream workup is selected. This reactor inlet pressure is generally 0.005 to 1 MPa gage, preferably 0.01 to 0.5 MPa gage. Naturally, the gas pressure employed in the inlet region of the reactor falls substantially over the entire bed of catalyst.

The product gas stream g leaving the oxidative dehydrogenation comprises, as well as butadiene and n-butane not removed in process step E), also hydrogen, carbon oxides and water vapor. As secondary constituents, it may also comprise oxygen, inert gas such as nitrogen, methane, ethane, ethene, propane and propene, and oxygen-containing hydrocarbons, called oxygenates.

In general, the product gas stream g leaving the oxidative dehydrogenation comprises 2 to 40% by volume of butadiene, 5 to 80% by volume of n-butane, 0 to 15% by volume of 2-butenes, 0 to 5% by volume of 1-butene, 5 to 70% by volume of water vapor, 0 to 10% by volume of low-boiling hydrocarbons (methane, ethane, ethene, propane and propene), 0.1 to 15% by volume of hydrogen, 0 to 70% by volume of inert gas, 0 to 10% by volume of carbon oxides, 0 to 10% by volume of oxygen and 0 to 10% by volume of oxygenates, where the total amount of the constituents adds up to 100% by volume. Oxygenates may, for example, be furan, acetic acid, methacrolein, maleic anhydride, maleic acid, phthalic anhydride, propionic acid, acetaldehyde, acrolein, formaldehyde, formic acid, benzaldehyde, benzoic acid and butyraldehyde. In addition, traces of acetylene, propyne and 1,2-butadiene may be present.

If product gas stream g comprises more than minor traces of oxygen, a process stage H) for removal of residual oxygen from product gas stream g is generally conducted. The residual oxygen may be troublesome in that it can cause butadiene peroxide formation in downstream process steps and can act as an initiator for polymerization reactions.

Unstabilized 1,3-butadiene can form hazardous butadiene peroxides in the presence of oxygen. The peroxides are viscous liquids. The density thereof is higher than that of butadiene. Since they are also only of low solubility in liquid 1,3-butadiene, they settle out on the base of storage vessels. In spite of their relatively low chemical reactivity, the peroxides are very unstable compounds which can decompose spontaneously at temperatures between 85 and 110° C. A particular hazard is that of the high shock sensitivity of the peroxides, which explode with the intensity of an explosive.

The risk of polymer formation exists particularly in the course of distillative removal of butadiene (steps L and M) and can lead therein to deposits of polymers (formation of what is called "popcorn") in the columns.

Preference is given to performing the oxygen removal H) immediately after the oxidative dehydrogenation G). In general, a catalytic combustion stage is conducted for this purpose, in which oxygen is reacted with hydrogen added in this stage in the presence of a catalyst. This hydrogen can be withdrawn from process stage D) as part of stream d2. This achieves a reduction in the oxygen content down to small traces.

A suitable catalyst for the oxidation of hydrogen comprises, supported on α-alumina, 0.01 to 0.1% by weight of platinum and 0.01 to 0.1% by weight of tin, based on the total weight of the catalyst. Platinum and tin are used advantageously in a weight ratio of 1:4 to 1:0.2, preferably in a ratio of 1:2 to 1:0.5, especially in a ratio of approximately 1:1. The catalyst advantageously comprises 0.05 to 0.09% by weight of platinum and 0.05 to 0.09% by weight of tin, based on the total weight of the catalyst. As well as platinum and tin, alkali metal and/or alkaline earth metal compounds can optionally be used in amounts of less than 2% by weight, especially less than 0.5% by weight. More preferably, the alumina catalyst comprises exclusively platinum and tin as active metals. The α-alumina catalyst support advantageously has a BET surface area of 0.5 to 15 $m^2/g$, preferably 2 to 14 $m^2/g$, especially 7 to 11 $m^2/g$. The support used is preferably a shaped body. Preferred geometries are, for example, tablets, annular tablets, spheres, cylinders, star extrudates or cog-shaped extrudates having diameters of 1 to 10 mm, preferably 2 to 6 mm. Particular preference is given to spheres or cylinders, especially cylinders.

The catalytic oxygen removal can in principle be performed in all reactor types and modes of operation known from the prior art, for example in a fluidized bed, in a staged furnace, in a fixed bed tubular reactor or shell and tube reactor, or in a plate heat exchanger reactor.

A further embodiment of the invention is the performance of this catalytic reaction together with the oxidative dehydrogenation in process step G in one reactor with 2 catalysts, and optional intermediate feeding of the combustion gas downstream of the dehydrogenation bed.

In process stage I), the gas stream h is preferably first cooled. The compressed gas is cooled with heat exchangers, which may be designed, for example, as shell and tube, spiral or plate heat exchangers. The heat removed is preferably utilized for thermal integration in the process. Subsequently, in a preferred embodiment of process step I), water is removed from the product stream. The water is preferably removed in a quench. The quench additionally serves to remove oxygen-containing byproducts.

Subsequently, the gas stream h is compressed in at least one first compression stage and subsequently cooled, which condenses out at least one condensate stream i1 comprising water to leave a gas stream i2 comprising n-butane, 1-butene, 2-butenes, butadiene, with or without hydrogen, water vapor, small amounts of methane, ethane, ethene, propane and propene, carbon oxides and inert gases.

The compression can be effected in one or more stages. Overall, compression is effected from a pressure in the range from 1.0 to 4.0 bar to a pressure in the range from 3.5 to 20 bar. Each compression stage is followed by a cooling stage, in which the gas stream is cooled to a temperature in the range from 15 to 60° C. The condensate stream i1 may thus also comprise several streams in the case of multistage compression.

Condensate stream i1 consists generally to an extent of at least 80% by weight, preferably to an extent of at least 90% by weight, of water, and additionally comprises, to a minor extent, low boilers, $C_4$ hydrocarbons, oxygenates and carbon oxides.

Suitable compressors are, for example, turbo compressors, rotary piston compressors and reciprocating piston compressors. The compressors can be driven, for example, with an electric motor, an expander or a gas or steam turbine. Typical compression ratios (exit pressure:inlet pressure) per compressor stage are between 1.5 and 3.0, according to the design.

The compressed gas is cooled with heat exchangers, which may be designed, for example, as shell and tube, spiral or plate heat exchangers. The coolants used in the heat exchangers are cooling water or heat carrier oils. In addition, preference is given to using air cooling using blowers.

The stream i2 comprising butadiene, butenes, butane, hydrogen and inert gas, with or without carbon oxides and low-boiling hydrocarbons (methane, ethane, ethene, propane, propene), is supplied as a starting stream to step J), the workup.

In a preferred embodiment of the process according to the invention, the uncondensable or low-boiling gas constituents such as hydrogen, oxygen, carbon oxides, the low-boiling hydrocarbons (methane, ethane, ethene, propane, propene) and inert gas, such as nitrogen, are removed in an absorption/desorption cycle by means of a high-boiling absorbent to obtain a C4 product gas stream j1 which consists essentially of the $C_4$ hydrocarbons. In general, the $C_4$ product gas stream j1 consists to an extent of at least 80% by volume, preferably to an extent of at least 90% by volume and more preferably to an extent of at least 95% by volume of the $C_4$ hydrocarbons. Stream j1 consists essentially of n-butane, butenes such as 2-butenes, and butadiene.

For this purpose, in an absorption stage, product gas stream i2, after prior water removal, is contacted with an inert absorbent, and the $C_4$ hydrocarbons are absorbed in the inert absorbent to obtain absorbent laden with $C_4$ hydrocarbons and an off gas j2 comprising the other gas constituents. In a desorption stage, the $C_4$ hydrocarbons are released again from the absorbent.

The absorption stage in step J) can be performed in any desired, suitable absorption column known to those skilled in the art. The absorption can be effected by passing product gas stream i2 once through the absorbent. However, it can also be effected in columns or in rotary absorbers. In this case, it is possible to work in cocurrent, countercurrent or cross current. Preference is given to performing the absorption in countercurrent. Suitable absorption columns are, for example, tray columns with bubble-cap trays, centrifugal trays and/or sieve trays, columns with structured packings, for example sheet metal packings having a specific surface area of 100 to 1000 $m^2/m^3$, such as Mellapak® 250Y, and columns with random packing. Also useful, however, are trickle and spray towers, graphite block absorbers, surface absorbers such as thick layer and thin layer absorbers, and rotary columns, pan scrubbers, cross-spray scrubbers and rotary scrubbers.

In one embodiment of the invention, the stream comprising butadiene, butene, butane, hydrogen and/or nitrogen, with or without carbon dioxide, is fed to an absorption column in the lower region. In the upper region of the absorption column, the stream comprising solvent, with or without water, is supplied.

Inventive absorbents are octanes, nonanes, decanes, undecanes, dodecanes, tridecanes, tetradecanes, pentadecanes, hexadecanes, heptadecanes and octadecanes, or fractions which are obtained from refinery streams and comprise the linear alkanes mentioned as main components.

Suitable absorbents are additionally comparatively nonpolar organic solvents, for example aliphatic $C_8$- to $C_{18}$-alkenes, or aromatic hydrocarbons such as the middle oil fractions from paraffin distillation, or ethers with bulky groups, or mixtures of these solvents, to which a polar solvent such as 1,2-dimethyl phthalate may be added. Suitable absorbents are additionally esters of benzoic acid and phthalic acid with straight-chain $C_1$-$C_8$-alkanols, such as n-butyl benzoate, methyl benzoate, ethyl benzoate, dimethyl phthalate, diethyl phthalate, and what are called heat carrier oils such as biphenyl and diphenyl ether, chlorine derivatives thereof, and triarylalkenes. A suitable absorbent is a mixture of biphenyl and diphenyl ether, preferably in the azeotropic composition, for example the commercially available Diphyl®. This solvent mixture frequently comprises dimethyl phthalate in an amount of 0.1 to 25% by weight.

In a preferred embodiment, the solvent used for the absorption in step J) is an alkane mixture such as tetradecane (technical grade C14-C17 cut).

At the top of the absorption column, an off gas stream j2 is drawn off, which comprises essentially inert gas, carbon oxides, with or without butane, butenes such as 2-butenes and butadiene, with or without hydrogen and low-boiling hydrocarbons (methane, ethane, ethene, propane, propene) and water vapor. This stream j2 is supplied partially to process step G). It is thus possible to adjust the inlet stream of the ODH reactor to the desired C4 content.

The solvent stream laden with C4 hydrocarbons is introduced into a desorption column. According to the invention, all column internals known to those skilled in the art are suitable for this purpose. In one process variant, the desorption step is conducted by decompressing and/or heating the laden solvent. A preferred process variant is the addition of stripping steam and/or the supply of fresh steam in the bottom of the desorber. The $C_4$-depleted solvent can be supplied to a phase separation as a mixture together with the condensed steam (water), such that the water is separated out of the solvent. All apparatuses known to those skilled in the art are suitable for this purpose. It is additionally possible to utilize the water removed from the solvent for production of the stripping steam. Preference is given to using 70 to 100% by weight of solvent and 0 to 30% by weight of water, more preferably 80 to 100% by weight of solvent and 0 to 20% by weight of water, especially 85 to 95% by weight of solvent and 5 to 15% by weight of water.

The removal J) is generally not entirely complete, and so small amounts or even only traces of the further gas constituents, especially of the low-boiling hydrocarbons, may be present in the C4 product gas stream, according to the type of removal. The reduction in the volume flow rate which is also brought about by the removal J) lowers the burden on the downstream process steps.

The C4 product gas stream j1 consisting essentially of n-butane, butenes such as 2-butenes and butadiene comprises generally 20 to 80% by volume of butadiene, 20 to 80% by volume of n-butane, 0 to 10% by volume of 1-butene and 0 to 50% by volume of 2-butenes, where the total amount adds up to 100% by volume.

In one process part, K), the C4 product gas stream j1 is separated into a recycle stream k2 consisting essentially of n-butane and butenes, such as 2-butenes, and a stream k1 consisting essentially of butadiene, by extractive distillation. Stream k2 is preferably added to the feed gas stream in step A), and recycled (partly) into the absorption stage in process step D), extraction step E) and/or into process step G) (ODH reactor).

The extractive distillation K) can be performed, for example, as described in Erdöl and Kohle Erdgas—Petrochemie volume 34 (8), pages 343 to 346 or Ullmanns Enzyklopädie der technischen Chemie, volume 9, $4^{th}$ edition 1975, pages 1 to 18.

The extractive distillation is operated preferably at a bottom temperature in the range from 100 to 250° C., especially at a temperature in the range from 110 to 210° C., a top temperature in the range from 10 to 100° C., especially in the range from 20 to 70° C., and a pressure in the range from 1 to 15 bar, especially in the range from 3 to 8 bar. The extractive distillation column has preferably 5 to 70 theoretical plates.

In the extractive distillation, the stream comprising butenes, butadiene, butane, methylpyrrolidone and water is contacted with a stream comprising N-methylpyrrolidone and water as described above in an extractive distillation zone. The extractive distillation zone is generally configured in the form of one or more column(s), which comprise(s) trays, random packings or structured packings as internals. The extractive distillation zone has generally 10 to 70 theoretical plates in order that a sufficiently good separating action is achieved. The extraction column preferably has a rescrubbing zone in the top of the column. This rescrubbing zone serves for recovery of the N-methylpyrrolidone present in the gas phase by liquid hydrocarbon reflux, for which the top fraction is condensed beforehand. Typical temperatures at the top of the column are between 30 and 60° C.

The top product stream k2 of the extractive distillation column comprises essentially butane and butenes, and small amounts of butadiene, and is drawn off in gaseous or liquid form. In a preferred embodiment, the top product stream is condensed in order to remove carbon oxides such as $CO_2$. The liquid butane/butene stream can be recycled into the absorption column in process step A), D), E) and/or in stage G). As a result, this stream, together with the product gas from the first dehydrogenation stage which has been quenched, cooled, compressed and freed of condensate, is passed to the extractive distillation for separation of butanes and butenes.

This separation of butane and butene need not then be conducted alongside the butadiene removal in the second extractive distillation.

At the bottom of the extractive distillation column, a stream k1 comprising N-methylpyrrolidone, water, butadiene, and small proportions of butenes and butane is obtained, which is supplied to a distillation column L). In this column, butadiene is obtained via the top or as a side draw. At the bottom of the distillation column, a stream l1 comprising N-methylpyrrolidone and water is obtained, the composition of the stream comprising N-methylpyrrolidone and water corresponding to the composition as added to the extraction. The stream comprising N-methylpyrrolidone and water is preferably passed into the extractive distillation in process step K).

The extractive distillation is conducted preferably at a bottom temperature in the range from 90 to 250° C., especially at a temperature in the range from 90 to 210° C., a top temperature in the range from 10 to 100° C., especially in the range from 20 to 70° C., and a pressure in the range from 1 to 15 bar, especially in the range from 3 to 8 bar. The extractive distillation column preferably has 5 to 70 theoretical plates.

The distillation in process step L) is conducted preferably at a bottom temperature in the range from 100 to 300° C., especially in the range from 150 to 200° C., and a top temperature in the range from 0 to 70° C., especially in the range from 10 to 50° C. The pressure in the distillation column is preferably in the range from 1 to 10 bar. The distillation column has preferably 2 to 30 and especially 5 to 20 theoretical plates.

A further distillation in process step M serves for further purification of the butadiene and can be conducted according to the prior art.

The invention claimed is:

1. A process for preparing butadiene from n-butane, comprising the steps of
   A) providing a feed gas stream a comprising n-butane;
   B) feeding the feed gas stream a comprising n-butane into at least one first dehydrogenation zone and nonoxidatively catalytically dehydrogenating n-butane to obtain a gas stream b comprising n-butane, 1-butene, 2-butenes, butadiene and hydrogen, with or without water vapor, with or without carbon oxides and with or without inert gases;
   C) compressing in at least one first compression stage and cooling the gas stream b to obtain at least one condensate stream c1 comprising water and a stream c2 comprising butenes and butadiene, n-butane, hydrogen and water vapor, with or without carbon oxides and with or without inert gases;
   D) absorbing the stream c2 comprising butenes, butadiene, n-butane, hydrogen and water vapor, with or without inert gases and with or without carbon oxides, with a selective solvent mixture comprising 80 to 97% by weight of N-methylpyrrolidone and 3 to 20% by weight of water, to obtain a stream d1 comprising N-methylpyrrolidone, water, and butenes, butadiene and butane, with or without carbon dioxide, and a stream d2 comprising hydrogen, with or without inert gases and without butane, wherein stream d2 is recycled fully or partly into the first dehydrogenation zone B);
   E) extractively distilling the stream d1 with a selective solvent stream e1 comprising 80 to 97% by weight of N-methylpyrrolidone and 3 to 20% by weight of water, to separate the stream d1, into a stream e2 comprising N-methylpyrrolidone, water, and butane, butenes and butadiene, and a stream e3 comprising butane, with or without carbon oxides;
   F) distilling the stream e2 to give a stream e1 comprising N-methylpyrrolidone and water, and a stream f comprising butane, butenes, butadiene;
   G) feeding stream f and an oxygenous gas into at least one second dehydrogenation zone and oxidatively dehydrogenating 1-butene and 2-butenes to obtain a gas stream g comprising n-butane, unconverted 1-butene and 2-butenes, butadiene and water vapor, with or without carbon oxides, with or without hydrogen and with or without inert gases.

2. The process according to claim 1, wherein stream e1 is recycled fully or partly into the absorption stage D) and the extractive distillation zone E).

3. The process according to claim 1, wherein stream e3 is recycled fully or partly into stage A).

4. The process according to claim 1, wherein stage G) is followed by performance of the following stage H):
   H) removing the residual oxygen present in gas stream g by means of a catalytic incineration stage in which the oxygen is reacted with a portion of or all of the hydrogen d2 removed beforehand and/or additionally supplied hydrogen to obtain an oxygen-depleted stream h.

5. The process according to claim 1, wherein stage G) is followed by performance of the following stages I) to L):
   I) compressing in at least one first compression stage and cooling the gas stream g to obtain at least one condensate stream i1 comprising water and a gas stream i2 comprising n-butane, 1-butene, 2-butenes, butadiene, hydrogen and water vapor, with or without carbon oxides and with or without inert gases;
   J) removing the uncondensable and low-boiling gas constituents comprising hydrogen, oxygen, carbon oxides, the low-boiling hydrocarbons methane, ethane, ethene, propane, propene and inert gases as gas stream j2 from gas stream i2 to obtain a C4 product gas stream j1 consisting essentially of C4 hydrocarbons;
   K) separating gas stream j1 by extractive distillation with a selective solvent into a stream k1 comprising butadiene and selective solvent and a stream k2 comprising n-butane, butenes and water vapor, with or without inert gases;

L) distilling stream k1 to give a stream l1 comprising selective solvent and water, and a stream l2 comprising butadiene.

6. The process according to claim 5, wherein stage L) is followed by performance of the following stage M):
- M) purifying distillation of the stream l2 comprising butadiene in one or two columns, in which a stream m2 comprising butadiene is obtained and a gas stream m1 comprising more volatile impurities than butadiene and/or a bottom stream m3 comprising less volatile impurities than butadiene is/are removed.

7. The process according to claim 5, wherein gas stream j2 is recycled fully or partly into the second dehydrogenation zone G).

8. The process according to claim 5, wherein stream k2 is recycled fully or partly into the feed stream in stage A), absorption stage D), extraction stage E) and/or partly the second dehydrogenation zone G).

9. The process according to claim 5, wherein the removal in stage J) is effected in two stages, by absorption with subsequent desorption.

10. The process according to claim 5, wherein stream l1 is recycled fully or partly into stage K).

11. The process according to claim 1, wherein the nonoxidative catalytic dehydrogenation of n-butane is performed autothermally with feeding of an oxygenous gas.

12. The process according to claim 11, wherein the oxygenous gas fed in is air or oxygen-enriched air, or the oxygenous gas fed in is oxygen of technical grade purity.

13. The process according to claim 1, wherein the feed stream a comprising n-butane is obtained from liquefied petroleum gas (LPG).

14. The process according to claim 1, wherein an additional butenic feed stream is fed into stage G).

15. A process for preparing butenes from n-butane, in which process steps A) to F) are conducted according to claim 1.

16. The process according to claim 4, wherein stage H) is followed by performance of the following stages I) to L):
- I) compressing in at least one first compression stage and cooling the oxygen-depleted stream h to obtain at least one condensate stream i1 comprising water and a gas stream i2 comprising n-butane, 1-butene, 2-butenes, butadiene, hydrogen and water vapor, with or without carbon oxides and with or without inert gases;
- J) removing the uncondensable and low-boiling gas constituents comprising hydrogen, oxygen, carbon oxides, the low-boiling hydrocarbons methane, ethane, ethene, propane, propene and inert gases as gas stream j2 from gas stream i2 to obtain a C4 product gas stream j1 consisting essentially of C4 hydrocarbons;
- K) separating gas stream j1 by extractive distillation with a selective solvent into a stream k1 comprising butadiene and selective solvent and a stream k2 comprising n-butane, butenes and water vapor, with or without inert gases;
- L) distilling stream k1 to give a stream l1 comprising selective solvent and water, and a stream l2 comprising butadiene.

* * * * *